United States Patent

Abe et al.

[11] Patent Number: 5,886,172
[45] Date of Patent: Mar. 23, 1999

[54] CARBAPENEM-3-CARBOXYLIC ACID ESTER DERIVATIVES

[75] Inventors: Takao Abe, Sakado; Toshio Kumagai, Kawagoe, both of Japan

[73] Assignee: Lederle (Japan) Ltd., Tokyo, Japan

[21] Appl. No.: 875,131

[22] PCT Filed: Dec. 4, 1996

[86] PCT No.: PCT/JP96/03540

§ 371 Date: Jul. 17, 1997

§ 102(e) Date: Jul. 17, 1997

[87] PCT Pub. No.: WO97/21712

PCT Pub. Date: Jun. 19, 1997

[30] Foreign Application Priority Data

Dec. 8, 1995 [JP] Japan .................................. 7-345076

[51] Int. Cl.$^6$ .......................... C07D 477/20; A61K 31/40
[52] U.S. Cl. .............................................................. 540/350
[58] Field of Search ............................................... 540/350

[56] References Cited

FOREIGN PATENT DOCUMENTS

| 0 160 391 | 11/1985 | European Pat. Off. . |
|---|---|---|
| 337637 | 10/1989 | European Pat. Off. . |
| 632039 | 1/1995 | European Pat. Off. . |
| 06157532 A | 6/1994 | Japan . |
| 08253482 A | 10/1996 | Japan . |

OTHER PUBLICATIONS

Kawamoto, Chem. Abs 121: 179400, 1994.
Mihara, Chem Abs 126: 31219, 1996.

*Primary Examiner*—Mark L. Berch
*Attorney, Agent, or Firm*—Testa, Hurwitz & Thibeault, LLP

[57] ABSTRACT

Disclosed are carbapenem-3-carboxylic acid ester derivatives of formula (I), wherein $R^1$ is a hydrogen atom or a lower alkyl group, $R^2$ is an alkyl group which may be substituted by a cycloalkyl group having about 4 to 7 carbon atoms and which may be substituted by a lower alkyl group, or is a cycloalkyl group having 4 to 7 carbon atoms which may be substituted by a lower alkyl group and n is 0 or 1. The compounds are highly absorbable through the digestive tract and are rapidly converted in the body to the active compound, which shows strong antibacterial activity.

2 Claims, No Drawings

CARBAPENEM-3-CARBOXYLIC ACID ESTER DERIVATIVES

This application is a 371 of PCT/JP96/03540, filed Dec. 04, 1996.

1. Technical Field

The present invention relates to orally administrable carbapenem antibiotics and, more particularly, to carbapenem-3-carboxylic acid ester derivatives which are highly absorbable through digestive tract.

2. Background Art

Heretofore, there have been proposed a lot of carbapenem compounds having a strong antibacterial activity. For example, Japanese Patent Kokai No. 202886/1985 discloses a carbapenem-3-carboxylic acid derivative having (N-methylacetoimidoyl-azetidin-3-yl)thio group at the 2-position represented by the following formula (A):

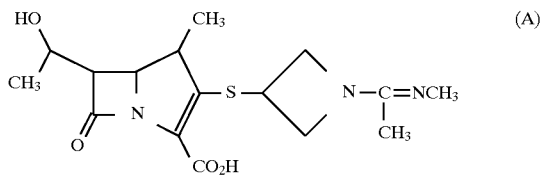

The inventors of the present invention also disclosed carbapenem derivatives having a methyl group introduced at the 1-position in the beta-configuration and (1-heterocyclyl-azetidin-3-yl)thio group at the side chain of the 2-position as represented by the formula (B) below, which showed a high antibacterial activity, a strong action of inhibiting beta-lactamase as well as improved resistance to kidney dehydropeptidase (Japanese Patent Kokai No. 53453/1996):

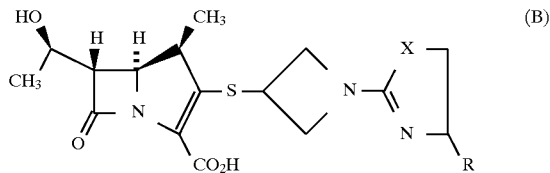

Because of poor absorbability through digestive tract, however, most of the carbapenem compounds proposed so far, including the compounds of the formulae (A) and (B) above, are clinically thought to be administrable as an injection only.

In clinical practice, however, it is desirable that a suitable administration route can be selected case by case in view of the purpose of therapy or circumstances on the side of patients. Compared with injections, oral drugs are especially preferable and clinically quite useful since they can be taken easily and conveniently, even in a patient's own home. Accordingly, there have been strong demands for the development of orally administrable carbapenem compounds which have a wide range of antibacterial spectrum and strong antibacterial activity.

DISCLOSURE OF INVENTION

Through extensive investigations, the present inventors discovered that an ester derivative produced by esterifying the carboxyl group at the 3-position of the compound represented by the following formula (II):

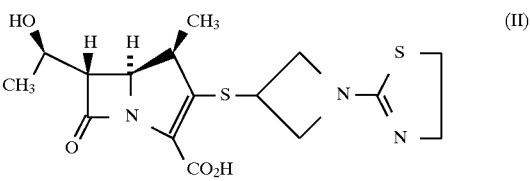

which is one of the compounds of formula (B) wherein the R is a hydrogen atom and the X is a sulfur atom, was highly absorbable through digestive tract and that the ester derivative was rapidly hydrolyzed in the body and thereby returned to the compound of formula (II). Consequently, the present inventors found that said ester derivative, as a pro-drug of the compound of formula (II), can be a clinically excellent antibiotic which can be administered orally.

Accordingly, the present invention provides (1R, 5S,6S)-2-[(1-(1,3-thiazolin-2-yl)azetidin-3-yl)thio]-6-[(R)-1-hydroxyethyl]-1-methyl-carbapen-2-em-3-carboxylic acid ester derivatives represented by the following formula (I):

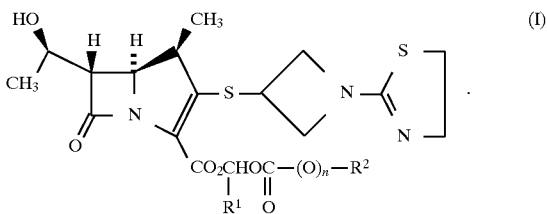

wherein
$R^1$ is a hydrogen atom or a lower alkyl group;
$R^2$ is an alkyl group which may be substituted by a cycloalkyl group having 4 to 7 carbon atoms which may further be substituted by a lower alkyl group, or a cycloalkyl group having 4 to 7 carbon atoms which may be substituted by a lower alkyl group; and,
n is 0 or 1.

More specifically, the present invention provides the respective compounds of formula (I) wherein:
$R^1$ is a hydrogen atom;
$R^1$ is an lower alkyl group;
$R^2$ is an alkyl group;
$R^2$ is an alkyl group substituted by a cycloalkyl group having 4 to 7 carbon atoms which may further be substituted by an lower alkyl group;
$R^2$ is a cycloalkyl group having 4 to 7 carbon atoms which may be substituted by a lower alkyl group;
n is 0; or n is 1.

Most specifically, the present invention provides (1-methylcyclohexanecarboxy)methyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate represented by the following formula (I-a):

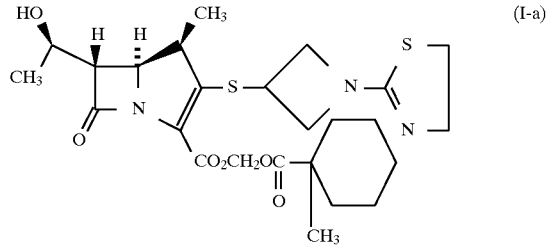

The compound of formula (I-a) is excellent both in physical stability and chemical stability, and is highly absorbable through digestive tract when administered orally. This compound is rapidly hydrolyzed in the body to turn to the active compound (II) to show a strong antibacterial activity. Therefore, its usefulness is superior to that of other carbapenem antibiotics proposed so far.

The present invention is described in more detail in the following.

The term "lower", used throughout the present specification and claims to qualify a group or a compound, means that the group or the compound so qualified has 1 to 7, preferably 1 to 4, carbon atoms.

The term "alkyl group" stands for a linear or branched alkyl group having 1 to 20 carbon atoms, e.g., methyl, ethyl, n-propyl, isopropyl, n-butyl, isobutyl, sec-butyl, tert.-butyl, n-pentyl, isopentyl, n-hexyl, isohexyl, n-heptyl, isoheptyl, octyl, isooctyl, nonanyl, dodecanyl, pentadecanyl, eicosanyl and so on.

The term "lower alkyl group" stands for an alkyl group having 1 to 7, preferably 1 to 4, carbon atoms. Examples thereof include methyl, ethyl, n-propyl, isopropyl, n-butyl, isobutyl, sec-butyl, and tert.-butyl.

The term "cycloalkyl group having 4 to 7 carbon atoms" stands for a saturated monocyclic hydrocarbon group having 4 to 7 ring carbon atoms. Examples thereof include cyclobutyl, cyclopentyl, cyclohexyl and cycloheptyl, and, among these, cyclopentyl and cyclohexyl are preferable. These cycloalkyl groups may be substituted by a lower alkyl group such as those mentioned above, e.g., methyl, ethyl, etc.

When the compounds of the present invention have an asymmetric carbon atom at the side chain of the 3-position, the isomers can be stereo-selectively obtained by using optically active starting materials, and each isomer can be isolated from the stereoisomeric mixture by usual method. Therefore, each isomer per se, as well as the stereoisomeric mixture, should be included in the compounds of the present invention.

The compounds of formula (I) can be prepared by the following reaction scheme:

The reaction of the compound of formula (II) with the compound of formula (III) can be carried out in an inert solvent selected from among ether type solvent such as diethyl ether, tetrahydrofuran and dioxan; hydrocarbon type solvent such as benzene, toluene, xylene and cyclohexane; halogenated hydrocarbon type solvent such as dichloromethane and chloroform; N,N-dimethylformamide, acetonitrile, dimethylsulfoxide, and so on, among which dimethylformamide is preferable, in the presence of suitable bases and quaternary ammonium salts.

Examples of the bases to be used in the above reaction include alkaline metal hydrides such as lithium hydride and sodium hydride; alkaline metal hydroxides such as sodium hydroxide and potassium hydroxide; alkaline metal carbonates such as sodium carbonate and potassium carbonate; alkaline metal hydrogencarbonates such as sodium hydrogencarbonate and potassium hydrogencarbonate; alkaline metal alkyls such as methyllithium and n-butyl-lithium; and organic amines such as trimethylamine, triethylamine, N,N-diisopropyl-N-ethylamine, pyridine and N,N-dimethylaminopyridine. Examples of the quaternary ammonium salts include triethylbenzylammonium chloride, tetraethylammonium chloride, tetrabutylammonium chloride and tetrabutylammonium bromide.

The amount of the compound of formula (III) to be used in the above reaction is not especially limited. Normally, the compound may be used at the proportion of about 1 to about 3 moles, preferably about 1 to about 2 moles, per mole of the compound of formula (II). The amounts of the bases and the quaternary ammonium salts are not especially limited, either, and may be changed appropriately according to the species of the bases and the quaternary ammonium salts used. Normally, they may be used at the proportion of about 1 to about 3 moles, respectively, per mole of the compound of formula (II). The reaction temperature is not strictly limited and may vary in a wide range. It may range generally from about −20° C. to about 75° C. The reaction may be completed in about 10 minutes to several hours.

The reaction described above provides the compound of formula (I). If necessary, the compound may be isolated and

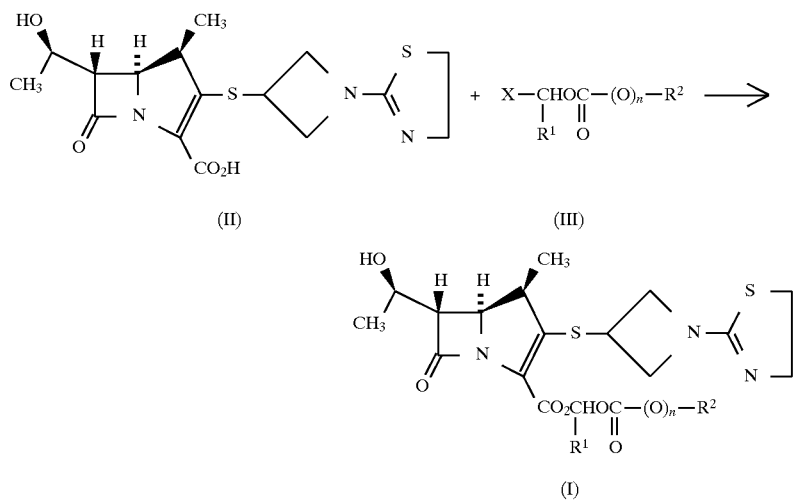

wherein X is a halogen atom, and $R^1$, $R^2$ and n have the same meanings as above.

A "halogen atom" includes chlorine, iodine, bromine and fluorine atoms, and, among these, chlorine, iodine and bromine atoms are preferable.

purified by subjecting the reaction mixture to ordinary means such as filtration, decantation, extraction, washing, removal of the solvent, column or thin-layer chromatography, recrystallization, distillation, and sublimation.

The compound of formula (I) may also be converted into a pharmaceutically acceptable acid addition salt thereof with organic or inorganic acids. Examples of organic acids include lower aliphatic acids such as formic acid, acetic acid, propionic acid, butyric acid, trifluoroacetic acid and trichloroacetic acid; polybasic acids such as succinic acid, citric acid and tartaric acid; amino acids such as aspartic acid and glutamic acid, substituted or unsubstituted benzoic acids such as benzoic acid and p-nitrobenzoic acid; lower-(halo) alkylsulfonic acids such as methanesulfonic acid and trifluoromethane-sulfonic acid; substituted or unsubstituted aryl sulfonic acids such as benzenesulfonic acid, p-nitrobenzenesulfonic acid, p-bromobenzenesulfonic acid, toluenesulfonic acid and 2, 4, 6-triisopropylbenzenesulfonic acid; and organic phosphoric acids such as diphenylphosphoric acid. Examples of inorganic acids include hydrochloric acid, sulfuric acid, hydrobromic acid, hydroiodic acid, fluoroboric acid, perchloric acid, nitric acid and phosphoric acid.

The compound of formula (II) to be used as the starting material in the above-mentioned reaction is a novel compound and can be prepared in accordance with the method described later in Preparation 6. As for the compound of formula (III), a compound known per se may be used, or the compound is easily obtainable from a known compound by such means as described later in Preparations 1 through 5.

As mentioned before, the carbapenem-3-carboxylic acid derivatives of formula (I) according to the present invention are orally administrable owing to their high absorbability through digestive tract. Furthermore, the compounds of formula (I) are rapidly converted into the active compound of formula (II) in the body, thereby exerting a strong antibacterial activity of this compound (See the results of the antibacterial activity test mentioned later.). The compounds of formula (I) are therefore expected to be clinically highly useful as a pro-drug to permit oral administration of the compound of formula (II).

The compounds of formula (I) can be administered to man or other mammals in the form of an orally administrable composition containing an antibacterially effective amount of the compound. The dose may vary in a wide range according to the patient's age, weight and symptom, doctor's diagnosis, etc. A normal dose range for adults, however, may be about 100–3000 mg/day which may be administered at one time or divided into several times a day.

The orally administrable compositions containing the compounds of the present invention can be prepared by using organic or inorganic carriers or diluents commonly used in preparing medicinal preparations, particularly antibiotic preparations, including excipients such as starch, lactose, white sugar, crystalline cellulose and calcium hydrogen phosphate; binders such as acacia, hydroxypropylcellulose, alginic acid, gelatin and polyvinyl pyrrolidone; lubricants such as stearic acid, magnesium stearate, calcium stearate, talc and hydrogenated plant oil; disintegrators such as modified starch, calcium carboxymethyl cellulose and low substituted hydroxypropylcellulose; and solution adjuvants such as non-ionic surface active agent and anionic surface active agent. Examples of the formulations of the composition include solid formulations such as tablets, coatings, capsules, troches, powders, fine powders, granules and dry syrups; and liquid formulations such as syrups.

The production of the carbapenem compounds of the present invention is described in more detail in the following by way of working examples. The present invention, however, is not limited to the following examples.

In the description of the examples, the symbols listed below are used to have the particular meanings respectively.
Ac: acetyl group
PNB: p-nitrobenzyl group preparation 1

$(CH_3)_2CH-CO_2H \longrightarrow (CH_3)_2CH-CO_2CH_2Cl$ (1) (2)

1.532 g of isovaleric acid (1), 5.04 g of $NaHCO_3$ and 0.518 g of tetrabutylammonium hydrogen sulfate were dissolved in a mixture solution of 50 ml of water and 50 ml of dichloromethane, and this mixture was ice-cooled. Then, to this mixture was added 3.025 g of chloromethylchlorosulfonate, and the reaction mixture was stirred for 0.5 hour at the same temperature and for 3 hours at room temperature. After the reaction, the organic layer was separated, washed with saturated saline solution and dried over magnesium sulfate. After removal of the solvent under reduced pressure, the resulting residue was purified by silica gel column chromatography (hexane: chloroform=3:1) to give 1.38 g (60%) of isovaleryloxy-methylchloride [Compound (2)].

$^1$H-NMR ($CDCl_3$) δ: 0.989 (d, 6H, J=6.59 Hz), 2.09–2.14 (m, 1H), 2.235 (d, 2H, J=6.60 Hz), 5.692 (s, 2H)

PREPARATION 2

The following compounds were obtained in substantially the same manner as that of Preparation 1.
2-Ethylbutyryloxymethylchloride [Compound (3)]
Yield: 36% $^1$H-NMR ($CDCl_3$) δ: 0.916 (t, 6H, J=7.59 Hz), 1.51–1.73 (m, 4H), 2.23–2.33 (m, 1H), 5.730 (s, 2H)
n-Octanoyloxymethylchloride [Compound (4)]
Yield: 87%
$^1$H-NMR ($CDCl_3$) δ: 0.79–0.83 (m, 3H), 1.21–1.23 (m, 8H), 1.53–1.61 (m, 2H), 2.29–2.34 (m, 2H), 5.636 (s, 2H)
n-Decanoyloxymethylchloride [Compound (5)]
Yield: 91%
$^1$H-NMR ($CDCl_3$) δ: 0.83–0.88 (m, 3H), 1.14–1.40 (m, 12H), 1.58–1.68 (m, 2H), 2.363 (t, 2H, J=7.59 Hz), 5.681 (s, 2H)
Cyclohexylacetoxymethylchloride [Compound (6)]
Yield: 83%
$^1$H-NMR ($CDCl_3$) δ: 0.84–1.00 (m, 2H), 1.06–1.28 (m, 3H), 1.55–1.79 (m, 6H), 2.194 (d, 2H, J=6.92 Hz), 5.632 (s, 2H)
(1-Methylcyclohexanecarboxy)methylchloride [Compound (7)]
Yield: quantitative
$^1$H-NMR ($CDCl_3$) δ: 1.14–1.67 (m, 8H), 1.198 (s, 3H), 2.02–2.08 (m, 2H), 5.736 (s, 2H)
4-Methylcyclohexanecarboxymethylchloride [Compound (8)]
Yield: quantitative
$^1$H-NMR ($CDCl_3$) δ: 0.895 (d, 0.9H, J=6.60 Hz), 0.905 (d, 2.1H, J=6.60 Hz), 1.42–1.80 (m, 7H), 1.96–2.05 (m, 2H), 2.22–2.37 (m, 0.3H), 2.53–2.67 (m, 0.7H), 5.701 (s, 0.6H), 5.730 (s, 1.4H)

PREPARATION 3

1-Cyclohexanecarboxyethylchloride [Compound (9)]

Compound (9) was obtained in accordance with the method described in J. Antibiotics 39, 1329–1342 (1986) (Yoshimura et al.).

$^1$H-NMR (CDCl$_3$) δ: 1.19–1.75 (m, 8H), 1.782 (d, 3H, J=5.94 Hz), 1.79–1.96 (m, 2H), 2.28–2.39 (m, 1H), 6.547 (q, 1H, J=5.94 Hz)

PREPARATION 4

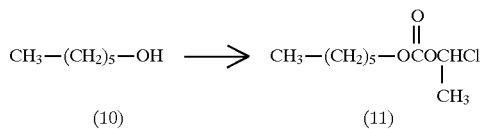

A mixture solution of 3.130 g of n-hexanol [Compound (10)] and 2.42 g of pyridine in 30 ml of dry dichloromethane was cooled to -78° C. To this mixture solution was added dropwise a solution of 4.289 g of 1-chloroethylchloroformate in 15 ml of dry dichloromethane for 1 hour. Then, the reaction mixture was stirred for 1.5 hour under ice-cooling and for 15 hours at room temperature. After the reaction, ethyl acetate was added to the reaction mixture. The organic layer was washed with 1N—HCl, saturated sodium bicarbonate aqueous solution and saturated saline solution respectively, and dried over magnesium sulfate. The solvent was removed under reduced pressure and the resulting residue was purified by silica gel column chromatography (hexane: chloroform=3:1) to give 5.697 g (91%) of 1-(n-hexyloxycarbonyloxy)ethyl-chloride [Compound (11)].

$^1$H-NMR (CDCl$_3$) δ: 0.823 (t, 3H, J=6.60 Hz), 1.16–1.49 (m, 6H), 1.59–1.67 (m, 2H), 1.763 (d, 3H, J=5.61 Hz), 4.11–4.16 (m, 2H), 6.362 (q, 1H, J=5.61 Hz)

PREPARATION 5

The following compounds were obtained in substantially the same manner as that of Preparation 4.

1-(n-Octyloxycarbonyloxy)ethylchloride [Compound (12)]

Yield: 94%

$^1$H-NMR (CDCl$_3$) δ: 0.811 (t, 3H, J=6.60 Hz), 1.21–1.33 (m, 10H), 1.57–1.67 (m, 2H), 1.763 (d, 3H, J=5.61 Hz), 4.11–4.16 (m, 2H), 6.362 (q 1, J=5.61 Hz)

1-(n-Decyloxycarbonyloxy)ethylchloride [Compound (13)]

Yield: 92%

$^1$H-NMR (CDCl$_3$) δ: 0.811 (t, 3H, J=6.93 Hz), 1.06–1.25 (m, 14H), 1.57–1.67 (m, 2H), 1.763 (d, 3H, J=5.94 Hz), 4.119 (q, 2H, J=6.60 Hz), 6.362 (q, 1H, J=5.94 Hz)

1-(n-Dodecyloxycarbonyloxy)ethylchloride [Compound (14)]

Yield: 95%

$^1$H-NMR (CDCl$_3$) δ: 0.79–0.84 (m, 3H), 1.19–1.48 (m, 18H), 1.57–1.67 (m, 2H), 1.764 (d, 3H, J=5.61 Hz), 4.09–4.16 (m, 2H), 6.33–6.40 (m, 1H)

PREPARATION 6

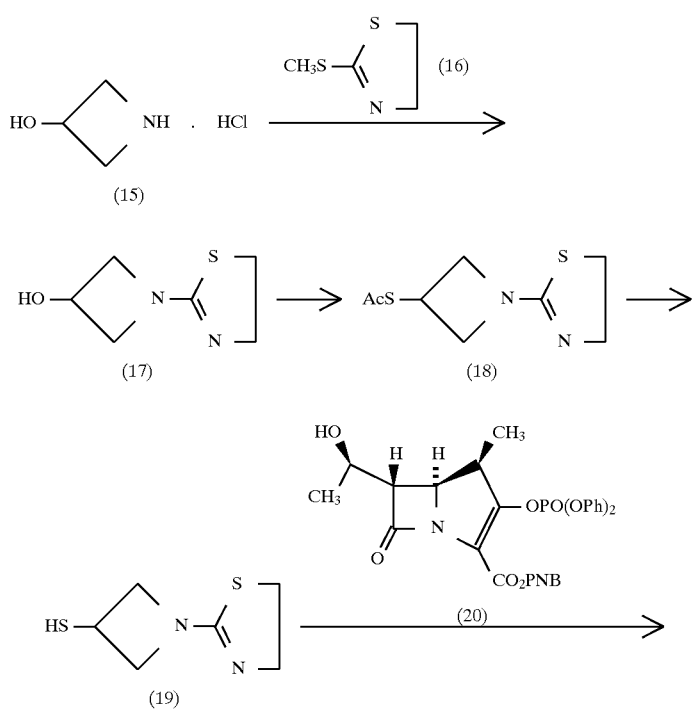

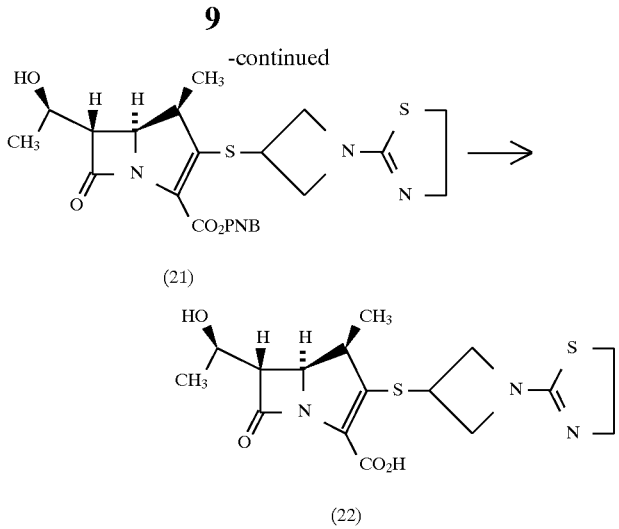

(a) To a solution of 109 mg of 3-hydroxyazetidine HCl [Compound (15)] in 5 ml of ethanol was added a mixture of 133 mg of 2-methylthiothiazoline [Compound (16)] and sodium methoxide (0.9 equivalent mole), and the reaction mixture was refluxed for 8 hours. After removal of the solvent under reduced pressure, the resulting residue was dissolved in chloroform and washed with saturated saline solution. After removal of the solvent under reduced pressure, the resulting residue was washed with diethylether to give 119 mg (81.5%) of 3-hydroxy-1-(thiazolin-2-yl) azetidine [Compound (17)] as crystals.

$^1$H-NMR (CDCl$_3$) δ: 3.356 (t, 2H, J=7.26 Hz), 3.70–4.00 (m, 4H), 4,211 (t, 2H, J=8.21 Hz), 4.622–4.705 (m, 1H), 4.971 (s, 1H)

(b) To a mixture solution of triphenylphosphine (2 equivalent moles) and diethyl azodicarboxylate (2 equivalent moles) in 10 ml of tetrahydrofuran was added a mixture of 119 mg Compound (17) obtained in the step (a) and thioacetic acid (2 equivalent moles) under ice-cooling, and the reaction mixture was stirred for 1 hour at the same temperature, then for 1 hour at room temperature. After the reaction solvent was removed under reduced pressure, the resulting residue was purified by silica gel column chromatography (chloroform: ethanol=19:1) to give 107 mg (65%) of 3-acetylthio-1-(thiazolin-2-yl)azetidine [Compound (18)].

$^1$H-NMR (CDCl$_3$) δ: 2.333 (s, 3H), 3.352 (t, 2H, J=7.26 Hz), 3.885 (dd, 2H, J=8.25 Hz, 5.28 Hz), 4.012 (t, 2H, J=7.26 Hz), 4.250–4.374 (m, 1H), 4.426 (t, 2H, J=8.25 Hz)

(c) 770 mg of 28% sodium methoxide-methanol solution was added to a mixture solution of 862 mg of Compound (18) obtained in the step (b) in 20 ml of anhydrous methanol under ice-cooling and nitrogen gas atmosphere. Then the reaction mixture was stirred for 10 minutes under the same conditions. After reaction, 4 ml of 2N—HCl was added to the reaction mixture and the solvent was removed under reduced pressure to give crude 3-mercapto-1-(thiazolin-2-yl)azetidine [Compound (19)]. Then the crude Compound (19) was dissolved in 15 ml of a mixture solution of anhydrous acetonitrile-chloroform and to this solution were added 2430 mg of p-nitrobenzyl (1R,5R,6S)-2-(diphenylphosphoryloxy)-6-[(R)-1-hydroxyethyl]-1-methyl-carbapen-2-em-3-carboxylate [Compound (20)] and 2.8 ml of diisopropylethylamine under ice-cooling and nitrogen gas atmosphere. After stirring the reaction mixture for 2 hours under the same conditions, ethyl acetate was added and the separated organic layer was washed with saturated sodium bicarbonate aqueous solution and saturated saline solution. The solvent was removed and the resulting residue was purified by silica gel column chromatography (chloroform: acetone =1:2) to give 1339 mg [65% yield from Compound (18)] of p-nitrobenzyl (1R,5S,6S)-2-[(1-(thiazolin-2-yl) azetidin-3-yl)thio]-6-[(R)-1-hydroxyethyl]-1-methyl-carbapen-2-em-3-carboxylate [Compound (21)].

$^1$H-NMR (CDCl$_3$) δ: 1.235 (d, 3H, J=7.26 Hz), 1.349 (d, 3H, J=6.27 Hz), 3.160 (quintet, 1H, J=7.26 Hz), 3.265 (dd, 1H, J=2.3 Hz, 6.26 Hz), 3.367 (t, 2H, J=7.26 Hz), 3.898–4.038 (m, 4H), 4.071–4.147 (m, 1H), 4.212–4.278 (m, 2H), 4.372 (2H, J=7.92 Hz), 5.255 & 5.517 (ABd, 2H, J=13.85 Hz), 7.665 (d, 2H, J=8.58 Hz), 8.226 (d, 2H, J=8.58 Hz)

(d) To a solution of 1339 mg of Compound (21) obtained in the step (c) in 20 ml of tetrahydrofuran were added 60 ml of 0.38 M phosphate buffer solution (pH=6.0) and 11.2 g of zinc powder, and the reaction mixture was vigorously stirred for 2 hours. After the reaction, unsolved substance was removed by using Celite (Trade name) and the filtrate was washed with ethyl acetate. After adjusting the pH of the filtrate to 5.5, the filtrate was concentrated and the resulting residue was purified by using Diaion HP-40 (Mitsubishi Kasei KK) column chromatography (5% isopropylalcohol-water) to give 630 mg (yield: 64%) of (1R,5S,6S)-2-[(1-(thiazolin-2-yl)azetidin-3-yl) thio]-6-[(R)-1-hydroxyethyl]-1-methyl-carbapen-2-em-3-carboxylic acid [Compound (22)].

$^1$H-NMR (D$_2$O) δ: 1.093 (d, 3H, J=6.93 Hz), 1.207 (d, 3H, J=6.27 Hz), 3.05–3.20 (m, 1H), 3.357 (dd, 1H, J=2.3 Hz, 5.94 Hz), 3.558 (t, 2H, J=7.26 Hz), 3.920 (t, 2H, J=7.26 Hz), 4.00–4.20 (m, 5H), 4.20–4.30 (m, 1H), 4.60–4.70 (m, 1H)
IR (KBr): 1740, 1640, 1590 cm$^{-1}$

EXAMPLE 1

Cyclohexylacetoxymethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (23)]

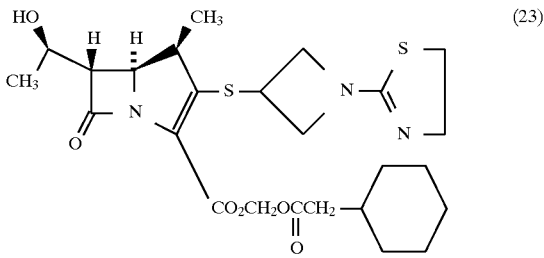

To a mixture solution of 1.917 g of Compound (22) obtained in the step (d) of Preparation 6, 2.278 g of triethylbenzylammonium chloride and 1.90 g of cyclohexylacetoxymethylchloride [Compound (6)] obtained in Preparation 2 were added 4.8 ml of dimethylformamide and 1.4 ml of triethylamine, and the reaction mixture was stirred for 4 hours at 45° C. After reaction, ethyl acetate was added to the reaction mixture and the organic layer was washed with saturated sodium bicarbonate aqueous solution and water. The solvent was removed under reduced pressure and the resulting residue was purified by silica gel column chromatography (dichloromethane-acetone) to give 2.044 g (yield: 76%) of Compound (23).

1H-NMR (CDCl$_3$) δ: 0.81–1.00 (m, 2H), 1.00–1.26 (m, 3H), 1.150 (d, 3H, J=7.25 Hz), 1.249 (d, 3H, J=6.27 Hz), 1.55–1.80 (m, 6H), 2.185 (d, 2H, J=6.93 Hz), 3.099 (quint., 1H, J=7.25 Hz), 3.149 (dd, 1H, J=2.31 Hz, 6.93 Hz), 3.76 (brs, 1H), 3.305 (t, 2H, J=7.59 Hz), 3.87–3.91 (m, 2H), 3.936 (t, 2H, J=7.59 Hz), 4.04–4.16 (m, 3H), 4.30–4.37 (m, 2H), 5.793 (d, 1H, J=5.6 Hz), 5.848 (d, 1H, J=5.61 Hz)

EXAMPLE 2

(1-Methylcyclohexanecarboxy)methyl (1R,5S,6S)-2[(1-(1,3-thiazolin-2-yl)azetidin-3-yl)thio]-6-[(R)-1-hydroxyethyl]-1-methyl-carbapen-2-em-3-carboxylate [Compound (24)]

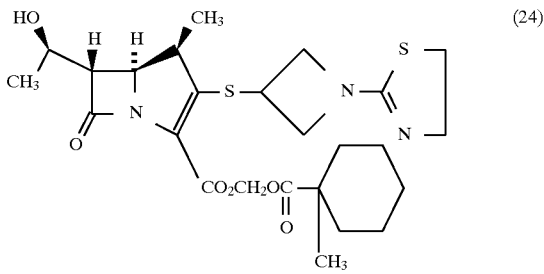

To a mixture solution of 4.45 g of Compound (22). 4H$_2$O obtained in the step (d) of Preparation 6, 4.56 g of triethylbenzylammonium chloride and 3.80 g of (1-methylcyclohexanecarboxy)methylchloride [Compound (7)] obtained in Preparation 2 in 9.4 ml of dimethylformamide was added 4.4 ml of diisopropylethylamine, and the reaction mixture was stirred for 4 hours at 45° C. After the reaction, ethyl acetate was added to the reaction mixture under ice-cooling and the pH of the mixture was adjusted to 4 by adding 1M citric acid solution. To the aqueous layer, ethyl acetate was added and the pH of the solution was adjusted to 7.6 by adding KHCO$_3$. The organic layer was washed with water and saturated saline solution, and was dried over magnesium sulfate. The solvent was removed under reduced pressure and the resulting residue was purified by silica gel column chromatography (dichloromethane-acetone) to give 9.47 g (yield: 88%) of Compound (24) in amorphous form.

Crystalline Compound (24)

5 ml of acetonitrile was added to 1.0 g of the amorphous Compound (24) obtained by the above procedure, and the resultant mixture was stirred for 1 hour. Being stirred, the mixture became homogeneous, and then crystals precipitated. The crystals were collected and washed with a small amount of acetonitrile, then dried in vacuum at room temperature to give 0.56 g of crystalline Compound (24).

1H-NMR (CDCl$_3$) δ: 1.13–1.54 (m, 8H), 1.186 (s, 3H), 1,221 (d, 3H, J=7.26 Hz), 1.333 (d, 3H, J=6.27 Hz), 2.02–2.11 (m, 2H), 2.405 (brs, 1H), 3.13–3.25 (m, 2H), 3.392 (t, 2H, J=7.59 Hz), 3.97–4.05 (m, 4H), 4.11–4.26 (m, 3H), 4.42–4.49 (m, 2H), 5.869 (d, 1H, J=5.61 Hz), 5.966 (d, 1H, J=5.61 Hz)

The crystalline Compound (24) was found to be crystalline by observation with a polarizing microscope, and showed characteristic peaks in powder X-ray diffractometry as shown in Table 1.

TABLE 1

| 2θ | d-Spacing(Å) | Intensity value | Intensity(I/I$_0$) |
|---|---|---|---|
| 9.360 | 9.44080 | 3969 | 50 |
| 11.240 | 7.86561 | 440 | 6 |
| 11.840 | 7.46832 | 586 | 8 |
| 13.520 | 6.54385 | 3315 | 42 |
| 14.140 | 6.25828 | 527 | 7 |
| 15.220 | 5.81654 | 1812 | 23 |
| 15.980 | 5.54158 | 6132 | 77 |
| 16.880 | 5.24809 | 2179 | 28 |
| 17.340 | 5.10989 | 8066 | 100 |
| 18.100 | 4.89701 | 1666 | 21 |
| 19.200 | 4.61886 | 1097 | 14 |
| 19.980 | 4.44027 | 3777 | 47 |
| 21.120 | 4.20310 | 1201 | 15 |
| 22.100 | 4.01888 | 1550 | 20 |
| 22.620 | 3.92765 | 2611 | 33 |
| 23.640 | 3.76045 | 1137 | 15 |
| 24.100 | 3.68970 | 785 | 10 |
| 25.320 | 3.51462 | 1594 | 20 |
| 25.700 | 3.46350 | 1117 | 14 |
| 27.720 | 3.21553 | 931 | 12 |
| 28.060 | 3.17734 | 1446 | 18 |
| 30.680 | 2.91171 | 1234 | 16 |
| 31.180 | 2.86614 | 999 | 13 |

EXAMPLE 3

Stability Test

Storage stability of (1-methylcyclohexane-carboxy)methyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (24)] was tested in comparison with its amorphous form and (cyclohexanecarboxy)methyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (C)], which is disclosed in European Patent Publication 632,039 A1.

Each compound in an amount of 20 mg was put in a glass bottle, and left to stand for 3 months in a constant-temperature chamber at 40° C. and at 40° C. /75% of humidity. The activity of each compound was assayed by HPLC after 1 month and 3 months, respectively. Assuming the activity at the beginning (initial day) to be 100%, the decrease in the activity is shown by percent residual activity in Table 2.

TABLE 2

| Compound | Condition | Residual activity (%) | | |
|---|---|---|---|---|
| | | Initial day | 1 month | 3 months |
| Compound (24) | 40° C. | 100 | 99.4 | 99.2 |
| (Crystalline) | 40° C./75% | 100 | 98.9 | — |
| Compound (24) | 40° C. | 100 | 67.5 | 36.8 |
| (Amorphous) | 40° C./75% | 100 | — | — |
| Compound (C) | 40° C. | 100 | 98.9 | 94.2 |
| (Crystalline) | 40° C./75% | 100 | 73.7 | — |

—: not tested

From the foregoing results, it is apparent that the crystalline form of Compound (24) retains its potency over a long period of time, whereas the amorphous form rapidly loses its potency.

EXAMPLE 4

The following compounds were prepared in substantially the same manner as that of Example 1 by using the compounds obtained in Preparations 1 to 5.

Isovaleryloxymethyl (1R,5S,6S)-2-[(1-(1,3-thiazolin-2-yl)-azetidin-3-yl)thio]-6-[(R)-1hydroxyethyl]-1-methyl-carbapen-2-em-3-carboxylate [Compound (25)]

Reaction temperature: 65° C. / Reaction time: 2 hours
Yield: 72%

1H-NMR (CDCl$_3$) δ: 0.931 (d, 6H, J=6.60 Hz), 1.190 (d, 3H, J=7.26 Hz), 1.287 (d, 3H, J=6.27 Hz), 2.01–2.15 (m, 1H), 2.231 (d, 2H, J=6.60 Hz), 3.09–3.17 (m, 1H), 3.192 (dd, 1H, J=2.31 Hz, 6.93 Hz), 3.348 (t, 2H, J=7.59 Hz), 3.91–3.96 (m, 2H), 3.977 (t, 2H, J=7.59 Hz), 4.08–4.21 (m, 3H), 4.387 (t, 2H, J=7.59 Hz), 5.831 (d, 1H, J=5.61 Hz), 5.898 (d, 1H, J=5.61 Hz)

2-Ethylbutyryloxymethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (26)]

Reaction temperature: 65° C. / Reaction time: 2 hours
Yield: 75%

$^1$H-NMR (CDCl$_3$) δ: 0.855 (t, 6H, J=7.59 Hz), 1.175 (d, 3H, J=7.26 Hz), 1.275 (d, 3H, J=6.27 Hz), 1.42–1.70 (m, 4H), 2.18–2.29 (m, 1H), 3.07–3.13 (m, 1H), 3.176 (dd, 1H, J=2.30 Hz, 6.59 Hz), 3.331 (t, 2H, J=7.59 Hz), 3.89–3.99 (m, 4H), 4.09–4.19 (m, 3H), 4.33–4.40 (m, 2H), 5.843 (d, 1H, J=5.61 Hz), 5.895 (d, 1H, J=5.6 Hz)

n-Octanoyloxymethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (27)]

Reaction temperature: 65° C. / Reaction time: 2 hours
Yield: 75%

$^1$H-NMR (CDCl$_3$) δ: 0.78–0.83 (m, 3H), 1.152 (d, 3H, J=7.25 Hz), 1.17–1.23 (m, 8H), 1.246 (d, 3H, J=6.27 Hz), 1.51–1.59 (m, 2H), 2.27–2.33 (m, 2H), 3.05–3.13 (m, 1H), 3.149 (dd, 1H, J=2.31 Hz, 6.60 Hz), 3.305 (t, 2H, J=7.59 Hz), 3.532 (brs, 1H), 3.87–3.96 (m, 4H), 4.04–4.17 (m, 3H), 4.31–4.37 (m, 2H), 5.787 (d, 1H, J=5.60 Hz), 5.859 (d, 1H, H=5.60Hz)

n-Decanoyloxymethyl (1R,5S,6S)-2-[(1-(1,3-thiazolin-2-yl)azetidin-3-yl)thio]-6-[(R)-1-hydroxyethyl]-1-methyl-carbapen- 2-em-3-carboxylate [Compound (28)]

Reaction temperature: 65° C. / Reaction time: 2 hours
Yield: 80%

$^1$H-NMR (CDCl$_3$) δ: 0.78–0.83 (m, 3H), 1.150 (d, 3H, J=7.25 Hz), 1.16–1.24 (m, 12H), 1.249 (d, 3H, J=6.27 Hz), 1.51–1.59 (m, 2H), 2.300 (t, 2H, J=7.59 Hz), 3.07–3.14 (m, 1H), 3.149 (dd, 1H, J=2.31 Hz, 6.60 Hz), 3.303 (t, 2H, J=7.59 Hz), 3.588 (brs, 1H), 3.87–3.96 (m, 4H), 4.04–4.17 (m, 3H), 4.22–4.37 (m, 2H), 5.785 (d, 1H, J=5.60 Hz), 5.860 (d, 1H, J=5.60 Hz)

4-Methylcyclohexanecarboxymethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (29)]

Reaction temperature: 45° C. / Reaction time: 4 hours
Yield: 80%

$^1$H-NMR (CDCl$_3$) δ: 0.878 (d, 0.9H, J=6.60 Hz), 0.894 (d, 2.1H, J=6.60 Hz), 1.221 (d, 3H, J=7.26 Hz), 1.335 (d, 3H, J=6.27 Hz), 1.34–1.80 (m, 7H), 1.96–2.05 (m, 2H), 2.23–2.28 (m, 0.3H), 2.450 (brs, 1H), 2.57–2.59 (m, 0.7H), 3.15–3.21 (m, 1H), 3.232 (dd, 1H, J=2.31 Hz, 6.60 Hz), 3.399 (t, 2H, J=7.59 Hz), 4.00–4.05 (m, 4H), 4.15–4.27 (m, 3H), 4.43–4.51 (m, 2H), 5.861 (d, 0.3H, J=5.61 Hz), 5.874 (d, 0.7H, 3=5.61 Hz), 5.940 (d, 0.3H, J=5.61 Hz), 5.953 (d, 0.7H, J=5.61 Hz)

1-Cyclohexanecarboxyethyl (1R,5S,6S)-2-[(1-(1,3-thiazolin-2-yl)azetidin-3-yl)thio]-6-((R)-1-hydroxyethyl]-1-methyl-carbapen-2-em-3-carboxylate [Compound (30)]

Reaction temperature: 45° C. / Reaction time: 4 hours
Yield: 74%

$^1$H-NMR (CDCl$_3$) δ: 1.20–1.73 (m, 17H), 1.89–1.93 (m, 2H), 2.26–2.63 (m, 2H), 3.13–3.25 (m, 2H), 3.39–3.46 (m, 2H), 4.02–4.11 (m, 4H), 4.12–4.27 (m, 3H), 4.49–4.59 (m, 2H), 6.94–7.00 (m, 1H)

1-(n-Hexyloxycarbonyloxy)ethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (31)]

Reaction temperature: 65° C. / Reaction time: 2 hours
Yield: 82%

1H-NMR (CDCl$_3$) δ: 0.79–0.84 (m, 3H), 1.148 (d, 3H, J=7.25 Hz), 1.16–1.26 (m, 9H), 1.51–1.62 (m, 5H), 3.04–3.16 (m, 2H), 3.300 (t, 2H, J=7.59 Hz), 3.85–3.96 (m, 4H), 4.05–4.14 (m, 5H), 4.30–4.37 (m, 2H), 6.77–6.84 (m, 1H)

1-(n-Octyloxycarbonyloxy)ethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (32)]

Reaction temperature: 65° C. / Reaction time: 2 hours
Yield: 83%

1H-NMR (CDCl$_3$) δ: 0.81–0.86 (m, 3H), 1.179 (d, 3H, J=7.26 Hz), 1.19–1.29 (m, 13H), 1.554 (d, 1.5H, J=4.95 Hz), 1.573 (d, 1.5H, J=4.95 Hz), 1.58–1.63 (m, 2H), 3.07–3.19 (m, 2H), 3.431 (t, 2H, J=7.59 Hz), 3.88–3.99 (m, 4H), 4.04–4.17 (m, 5H), 4.33–4.40 (m, 2H), 6.80–6.87 (m, 1H)

1-(n-Decyloxycarbonyloxy)ethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (33)]

Reaction temperature: 65° C. / Reaction time: 2 hours
Yield: 80%

$^1$H-NMR (CDCl$_3$) δ: 0.846 (t, 3H, J=6.93 Hz), 1.185 (d, 3H, J=7.26 Hz), 1.20–1.30 (m, 17H), 1.55–1.64 (m, 5H), 3.11–3.20 (m, 2H), 3.31–3.36 (m, 2H), 3.89–4.00 (m, 4H), 4.06–4.18 (m, 5H), 4.33–4.41 (m, 2H), 6.81–6.88 (m, 1H)

1-(n-Dodecyloxycarbonyloxy)ethyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate [Compound (34)]

Reaction temperature: 65° C. / Reaction time: 2 hours
Yield: 81%

1H-NMR (CDCl$_3$) δ: 0.849 (t, 3H, J=6.93 Hz), 1.17–1.31 (m, 24H), 1.55–1.63 (m, 5H), 3.08–3.20 (m, 2H), 3.31–3.36 (m, 2H), 3.89–4.00 (m, 4H), 4.06–4.18 (m, 5H), 4.34–4.41 (m, 2H), 6.81–6.88 (m, 1H)

Antibacterial activity test, pharmacological test and toxicity test were performed as mentioned below to verify the properties of the compounds of formula (I) according to the present invention.

I. Antibacterial Activity test

Test Procedure

Antibacterial activity was tested by using an agar plate dilution method in accordance with the standard method of the Japanese Chemotherapy Society [Chemotherapy, vol. 29, 76–79 (1981)].

Mueller-Hinton (MH) agar liquid media of the test microorganisms were cultured overnight at 37° C. and the resultant culture media were diluted with a buffered saline gelatin (BSG) solution to contain approximately $10^5$ cells of the test microorganisms per milliliter. Then, about 5 microliters each of the diluted solutions were inoculated on MH agar media containing the test compound by using a microplanter. After incubating the media at 37° C. for 18 hours, a minimum concentration of the test compound at which no growth of the test microorganisms was found was determined to be the minimum inhibitory concentration (MIC).

The test microorganism strains used in this test were all standard ones. The test compound used herein was Compound (22) obtained in Preparation 6, i.e., the compound of formula (II), which is the active metabolite of the compounds of formula (I).

Results

Table 3 shows the results. The results indicate that the test compound of formula (II), which is the active metabolite of the compounds of formula (I) according to the present invention, has a strong antibacterial activity especially against Staphylococcus, Streptococcus, Klebsiella and Proteus.

TABLE 3

MINIMUM INHIBITORY CONCENTRATIONS (MIC)

| Test Microorganisms | MIC ($\mu$g/ml) Test Compound (22) |
|---|---|
| S. aureus FDA209P JC-1 | 0.013 |
| S. aureus Terajima | ≦0.006 |
| S. aureus MS353 | ≦0.006 |
| S. pyogenes Cook | ≦0.006 |
| B. subtilis ATCC 6633 | 0.025 |
| M. luteus ATCC 9341 | 0.2 |
| E. coli NIHJ JC-2 | 0.013 |
| E. coli K-12 C600 | 0.1 |
| E. cloacae 963 | 0.05 |
| E. aerogenes ATCC 13048 | 0.1 |
| K. pneumoniae PCI-602 | 0.013 |
| S. typhimurium 11D971 | 0.025 |
| S. typhi 901 | ≦0.006 |
| S. paratyphi 1015 | 0.05 |
| S. schottmuelleri 8006 | 0.025 |
| S. enteritidis G14 | 0.39 |
| S. marcescens IAM 1184 | 0.05 |
| M. morganii IFO 3848 | 0.39 |
| P. mirabilis IFO 3849 | 0.39 |
| P. vulgaris OX-19 | 0.1 |
| P. vulgaris HX-19 | 0.1 |
| P. rettgeri IFO 3850 | 0.39 |

II. Pharmacological Test

Test procedures

Five-week-old male mice of ddY strain were used after fasting overnight. The test compounds in 1% physiological saline were orally administered to the mice at a dose of 100 mg/kg, and 0.4 ml blood was taken from the cervical vein of each mouse at 15, 30, 60 and 120 minutes after dosing. Blood concentrations of the test compounds were assayed and area under the concentration-time curve (AUC) was calculated.

The test compounds used herein were Compounds (23) through (34) obtained in Examples mentioned above. These compounds were administered to two mice/group, respectively.

Results

Table 4 shows the maximum concentrations (Cmax) and the AUCs. The data shown in the table are those of the compound of formula (II) because the test compounds were not detected at all but their active metabolite, i.e., the compound of formula (II) was only detected in the blood of the mice.

The results indicate that the compounds of the present invention are good in absorption through digestive tract.

TABLE 4

PHARMACOLOGICAL TEST (ORAL ADMINISTRATION)

| Test Compounds | Cmax ($\mu$g/ml) | AUC ($\mu$g · hr/ml) (0–∞) |
|---|---|---|
| (23) | 12.3 | 9.7 |
| (24) | 11.5 | 8.9 |
| (25) | 5.7 | 3.7 |
| (26) | 9.9 | 6.8 |
| (27) | 2.9 | 2.3 |
| (28) | 1.1 | 0.6 |
| (29) | 9.5 | 6.9 |
| (30) | 11.9 | 7.5 |
| (31) | 8.8 | 7.0 |
| (32) | 4.4 | 5.4 |
| (33) | 7.6 | 5.5 |
| (34) | 4.7 | 4.0 |

III. Toxicity Test

Toxicity test was performed in 7-week-old male rats of Wistar strain. Compounds (23) through (34) were orally administered to 3 rats/group, and the rats were observed for a week. As a result, all the rats given 1 g/kg dosing survived without any abnormal findings.

As mentioned hereinabove, the carbapenem compounds of formula (I) according to the present invention are well absorbed through digestive tract and are rapidly converted into the active compound of formula (II) in the body to permit exertion of the strong antibacterial activity. Accordingly, the compounds of formula (I) can be used as a pro-drug of the compound of formula (II).

The present invention therefore provides orally administrable carbapenem antibiotics which are highly useful in the treatment or prevention of infections caused by various pathogenic bacteria.

We claim:

1. A crystalline compound of (1-methylcyclohexanecarboxy)methyl (1R,5S,6S)-2-[(1-(1,3-thiazolin-2-yl)azetidin-3-yl)thio]-6-[(R)-1-hydroxyethyl]-1-methyl-carbapen-2-em-3-carboxylate represented by the following formula (I-a):

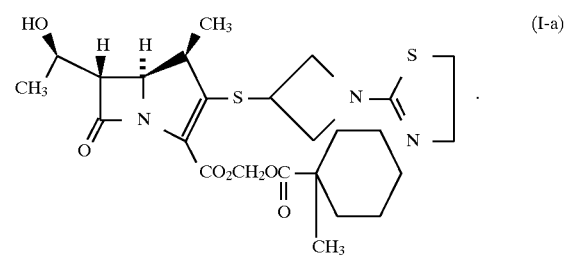

2. The compound according to claim 1 which has the following X-ray powder diffraction parameters:

| 2θ | d-Spacing(Å) | Intensity value | Intensity (I/I₀) |
| --- | --- | --- | --- |
| 9.360 | 9.44080 | 3969 | 50 |
| 11.240 | 7.86561 | 440 | 6 |
| 11.840 | 7.46832 | 586 | 8 |
| 13.520 | 6.54385 | 3315 | 42 |
| 14.140 | 6.25828 | 527 | 7 |
| 15.220 | 5.81654 | 1812 | 23 |
| 15.980 | 5.54158 | 6132 | 77 |
| 16.880 | 5.24809 | 2179 | 28 |
| 17.340 | 5.10989 | 8066 | 100 |
| 18.100 | 4.89701 | 1666 | 21 |
| 19.200 | 4.61886 | 1097 | 14 |
| 19.980 | 4.44027 | 3777 | 47 |
| 21.120 | 4.20310 | 1201 | 15 |
| 22.100 | 4.01888 | 1550 | 20 |
| 22.620 | 3.92765 | 2611 | 33 |
| 23.640 | 3.76045 | 1137 | 15 |
| 24.100 | 3.68970 | 785 | 10 |
| 25.320 | 3.51462 | 1594 | 20 |
| 25.700 | 3.46350 | 1117 | 14 |
| 27.720 | 3.21553 | 931 | 12 |
| 28.060 | 3.17734 | 1446 | 18 |
| 30.680 | 2.91171 | 1234 | 16 |
| 31.180 | 2.86614 | 999 | 13. |

\* \* \* \* \*